United States Patent
Truong et al.

(10) Patent No.: US 12,318,545 B2
(45) Date of Patent: Jun. 3, 2025

(54) CHAMBER ADAPTOR AND MANUFACTURING METHOD THEREOF

(71) Applicant: Telesair, Inc., Irvine, CA (US)

(72) Inventors: Hector Truong, Westminster, CA (US); Cheng Wang, Shenzhen (CN); Chi Wai Choy, Irvine, CA (US); Bo Li, San Diego, CA (US); Yong Liu, Westminster, CA (US)

(73) Assignee: Telesair, Inc., Irvine, CA (US)

( * ) Notice: Subject to any disclaimer, the term of this patent is extended or adjusted under 35 U.S.C. 154(b) by 0 days.

(21) Appl. No.: 17/969,978

(22) Filed: Oct. 20, 2022

(65) Prior Publication Data

US 2024/0131291 A1   Apr. 25, 2024
US 2024/0226489 A9   Jul. 11, 2024

(51) Int. Cl.
*A61M 16/00* (2006.01)
*A61M 16/10* (2006.01)
(Continued)

(52) U.S. Cl.
CPC ... *A61M 16/1095* (2014.02); *B29C 45/14008* (2013.01); *H05K 5/0026* (2013.01);
(Continued)

(58) Field of Classification Search
CPC .......... A61N 16/1075; A61M 16/1085; A61M 16/1095; A61M 16/024;
(Continued)

(56) References Cited

U.S. PATENT DOCUMENTS 3,367,186 A * 2/1968 Allen ................. G01K 7/24
374/165
5,031,612 A   7/1991 Clementi
(Continued)

FOREIGN PATENT DOCUMENTS

| CN | 104657776 B | 6/2018 |
| CN | 109616102 B | 8/2021 |
| CN | 112509036 B | 6/2022 |

OTHER PUBLICATIONS

International Search Report and Written Opinion issued on Mar. 3, 2023, in corresponding International Application No. PCT/US2022/050385, 8 pages.

*Primary Examiner* — Margaret M Luarca
*Assistant Examiner* — Sarah B Lederer
(74) *Attorney, Agent, or Firm* — Maier & Maier, PLLC

(57) ABSTRACT

A chamber adaptor and a manufacturing method thereof. The chamber adaptor includes: a housing provided with a gas inlet, a gas outlet, a chamber inlet, and a chamber outlet, where the gas inlet is configured to be removably connected to a main board device, the gas outlet is configured to be removably connected to a respiratory pathway, the chamber inlet is configured to be removably connected to an input end of a chamber for storing liquid and the chamber outlet is configured to be removably connected to an output end of the chamber, the chamber adaptor further includes a control circuit and at least one sensing apparatus, where the at least one sensing apparatus is arranged on one end of the control circuit closer to the gas outlet and extends into a gas output channel.

12 Claims, 4 Drawing Sheets

(51) Int. Cl.
*B29C 45/14* (2006.01)
*H05K 5/00* (2006.01)

(52) U.S. Cl.
CPC .............. *A61M 2016/0021* (2013.01); *A61M 2016/0039* (2013.01); *A61M 2016/0042* (2013.01); *A61M 16/024* (2017.08)

(58) Field of Classification Search
CPC .. A61M 2016/0021; A61M 2016/0039; B29C 45/14008; H05K 5/0026
See application file for complete search history.

(56) References Cited

U.S. PATENT DOCUMENTS

| | | | | |
|---|---|---|---|---|
| 8,701,662 | B2* | 4/2014 | Pujol | A61M 16/16 128/204.17 |
| 10,974,015 | B2* | 4/2021 | Stoks | A61M 16/1095 |
| 2001/0050080 | A1* | 12/2001 | Seakins | A61M 16/16 128/204.22 |
| 2002/0100320 | A1* | 8/2002 | Smith | A61M 16/16 73/431 |
| 2004/0245658 | A1 | 12/2004 | Niland et al. | |
| 2015/0027204 | A1* | 1/2015 | Stoks | G01K 1/14 73/31.05 |
| 2016/0287832 | A1 | 10/2016 | Cortez, Jr. et al. | |
| 2017/0151411 | A1* | 6/2017 | Osborne | G01K 13/02 |
| 2019/0275281 | A1 | 9/2019 | Creusot et al. | |
| 2021/0063217 | A1* | 3/2021 | Tsuchiya | G01F 1/688 |
| 2022/0273904 | A1* | 9/2022 | Kramer | A61M 16/109 |

* cited by examiner

CHAMBER ADAPTOR AND MANUFACTURING METHOD THEREOF

TECHNICAL FIELD

The present application relates to the technical field of medical treatment, and in particular, to a chamber adaptor and a manufacturing method thereof.

BACKGROUND

In recent years, a respiratory humidifier has been developed to facilitate a high flow oxygen therapy (HFOT). The respiratory humidifier plays a key role in operation of a HFOT system, which can be employed to provide respiratory support for a patient who is unable to ensure enough ventilation by their own respiratory efforts, for example, a patient who suffers from a respiratory disease caused by the COVID-19 virus.

The HFOT system functions to assist the patient with respiratory insufficiency by exchanging gas and energy (such as thermal energy) through the respiratory humidifier. Typically, oxygen, in conjunction with compressed air and humidification, is delivered to the patient through the respiratory humidifier at a flow rate higher than that delivered in traditional oxygen therapy.

This background information is provided to reveal information believed by the applicant to be of possible relevance to the present application. No admission is necessarily intended, nor should be construed, that any of the preceding information constitutes prior art against the present application.

SUMMARY

Embodiments of the present application provide a chamber adaptor and a manufacturing method thereof.

The foregoing and other objects are achieved by the subject matter of the independent claims. Further implementation forms are apparent from the dependent claims, the description and the figures.

A first aspect of the present application provides a chamber adaptor, including a housing provided with a gas inlet, a gas outlet, a chamber inlet, and a chamber outlet; where
  the gas inlet is configured to be removably connected to a main board device, the gas outlet is configured to be removably connected to a respiratory pathway, the chamber inlet is configured to be removably connected to an input end of a chamber for storing liquid and the chamber outlet is configured to be removably connected to an output end of the chamber;
  the chamber adaptor further includes a control circuit with at least one sensing apparatus connected to the control circuit;
  where the at least one sensing apparatus is arranged on one end of the control circuit closer to the gas outlet and extends into a gas output channel formed between the gas outlet and the chamber outlet, and the at least one sensing apparatus is configured to detect temperature information of gas passing through the gas output channel;
  where the other end of the control circuit is electrically connected to the main board device, and the control circuit is configured to deliver the temperature information detected by the at least one sensing apparatus to the main board device.

In a possible implementation, a length of the at least one sensing apparatus is within a predefined range.

In a possible implementation, the at least one sensing apparatus is a thermistor probe.

In a possible implementation, a heat transfer rate between the at least one thermistor probe and the housing is smaller than a heat transfer rate between the thermistor probe and the gas passing through the gas output channel.

In a possible implementation, the at least one sensing apparatus is connected to the control circuit through a connecting wire, and the connecting wire is arranged on the control circuit in an S shape.

In a possible implementation, the other end of the control circuit is provided with a preset number of conductive contacts, and the conductive contacts are on the top and the bottom of the control circuit, and the conductive contacts are exposed from the control circuit.

In a possible implementation, the other end of the control circuit is further provided with a first sealing element formed in a first molding process, and an area of the control circuit where the conductive contacts are located protrudes from the first sealing element.

In a possible implementation, the gas inlet is isolated from the gas outlet in such a manner that substantially no gas can directly go from the gas inlet to the gas outlet without passing by the chamber inlet and the chamber outlet.

In a possible implementation, the other end of the control circuit is provided with a second sealing element to fill a connection gap between the control circuit and the main board device.

In a possible implementation, the gas inlet is provided with a one-way valve.

In a possible implementation, the gas inlet is further provided with a third sealing element for preventing gas leakage.

In a possible implementation, the chamber inlet is a male connector or a female connector, and the chamber outlet is a male connector or a female connector.

A second aspect of the present application provides a method for manufacturing the chamber adaptor according to the first aspect, including:
  performing a first molding process to form the control circuit;
  performing a second molding process to form a first supporting element, a second supporting element and a third supporting element on the molded control circuit;
  where the first supporting element, the second supporting element and the third supporting element are plastic materials; and
  performing a third molding process to form the chamber adaptor by placing the control circuit with the first supporting element, the second supporting element and the third supporting element into a mold of the chamber adaptor.

The present application provides a chamber adaptor and a manufacturing method thereof. The chamber adaptor includes: a housing provided with a gas inlet, a gas outlet, a chamber inlet, and a chamber outlet, where the gas inlet is configured to be removably connected to a main board device, the gas outlet is configured to be removably connected to a respiratory pathway, the chamber inlet is configured to be removably connected to an input end of a chamber for storing liquid and the chamber outlet is configured to be removably connected to an output end of the chamber, the chamber adaptor further includes a control circuit and at least one sensing apparatus connected to the control circuit, where the at least one sensing apparatus is arranged on one end of the control circuit closer to the gas outlet and extends into a gas output channel formed between the gas outlet and the chamber outlet, and the at least one sensing apparatus is configured to detect temperature information of gas passing through the gas output channel, where the other end of the control circuit is electrically connected to the main board device, and the control circuit is configured to deliver the temperature information detected by the at least one sensing apparatus to the main board device.

BRIEF DESCRIPTION OF THE DRAWINGS

The accompanying drawings are used to provide a further understanding of the present application, constitute a part of the specification, and are used to explain the present application together with the following specific embodiments, but should not be construed as limiting the present application.

DETAILED DESCRIPTION OF THE EMBODIMENTS

In the following description, reference is made to the accompanying figures, which form part of the application, and which show, by way of illustration, specific aspects of embodiments of the present application or specific aspects in which embodiments of the present application may be used. It is understood that embodiments of the present application may be used in other aspects and include structural or logical changes not depicted in the figures. The following detailed description, therefore, is not to be taken in a limiting sense, and the scope of the present application is defined by the appended claims.

A high flow oxygen therapy (HFOT) system is widely used in the field of medical treatment. For example, when a patient suffers from a respiratory disease caused by the COVID-19 virus, the patient generally has trouble in ensuring enough ventilation by his own respiratory efforts. In such a case, the HFOT system can be employed to provide respiratory support for the patient having respiratory insufficiency. Specifically, a respiratory humidifier is provided in the HFOT system and plays an important role in the operation of the HFOT system. The respiratory humidifier specifically serves to deliver humidified and heated gas, consisted of oxygen and compressed air, to the patient at a flow rate higher than that delivered in traditional oxygen therapy, so as to alleviate discomfort of the patient caused by the respiratory disease.

However, in existing art, the respiratory humidifier is not specifically designed to ensure the accuracy of the temperature detection of the gas flowing through the respiratory humidifier, and errors in temperature detection may be caused by various factors, such as failure of the sensing apparatus, influence of the heat transferred from the housing on which the sensing apparatus is provided, etc. Therefore, the present application provides a chamber adaptor to solve the above mentioned problems.

In the following, the technical solutions of the present application will be described in detail with reference to the accompanying drawings.

Figure 1:
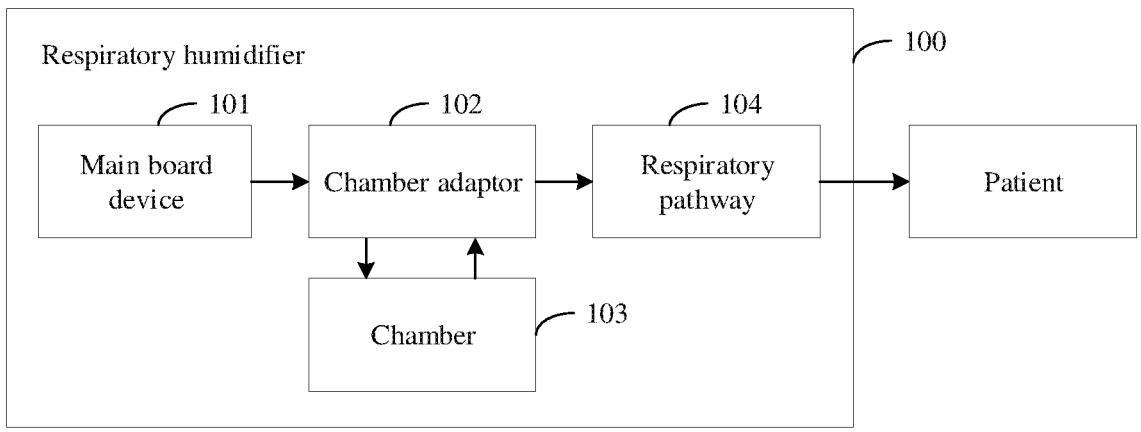
FIG. 1 shows a schematic block diagram of a respiratory humidifier provided by an embodiment of the present application.

FIG. 1 shows a schematic block diagram of a respiratory humidifier provided by an embodiment of the present application.

As shown in FIG. 1, the respiratory humidifier 100 includes a main board device 101, a chamber adaptor 102, a chamber 103 and a respiratory pathway 104. The respiratory humidifier 100 serves to deliver humidified and heated oxygen, in conjunction with compressed air, to the patient at a flow rate higher than that delivered in traditional oxygen therapy. It is to be noted that the arrows between different blocks in FIG. 1 represent a one-way flow path of the gas within the humidifier.

The main board device 101 is configured to provide oxygen and compressed air to the chamber adaptor 102 for further processing. In a possible implementation, the main board device also serves to control the operating of the respiratory humidifier, for example, the main board device can adjust the operating parameters of the respiratory humidifier 100, and process the data feedback by other components of the respiratory humidifier 100. In a possible implementation, the main board device includes a gas provider configured to perform the function of providing the oxygen and the compressed air.

The chamber adaptor 102 is configured to direct the gas to flow along a predefined pathway inside the respiratory humidifier 100. Specifically, the gas flowing inside the respiratory humidifier 100 is directed from the main board device 101 to the chamber 103 through the chamber adaptor 102 first, and then the gas is directed from the chamber 103 to the respiratory pathway 104 through the chamber adaptor 102, and finally the gas is delivered to the patient after it finishes its journey in the respiratory pathway 104.

The chamber 103 is configured to store liquid for humidifying the gas flowing through the chamber 103. In a possible implementation, the liquid may be water. In a possible implementation, a floater is provided within the chamber 103 for controlling the liquid level inside the chamber. Specifically, as the liquid is injected into the chamber, the liquid level inside the chamber rises, which also causes the position of the floater to rise. And when the floater rises to a preset height, the liquid injection port of the chamber 103 is closed, and the liquid level stops to rise.

The respiratory pathway 104 is used to guide the gas flowing from the chamber adaptor 102 to the patient. In a possible implementation, a heating element is provided inside the chamber for gas heating, and a heating wire is provided inside the respiratory pathway to preserve the temperature of the heated gas. After being humidified and heated in the chamber 103, the gas is delivered to the patient for medical treatment.

Figure 2:
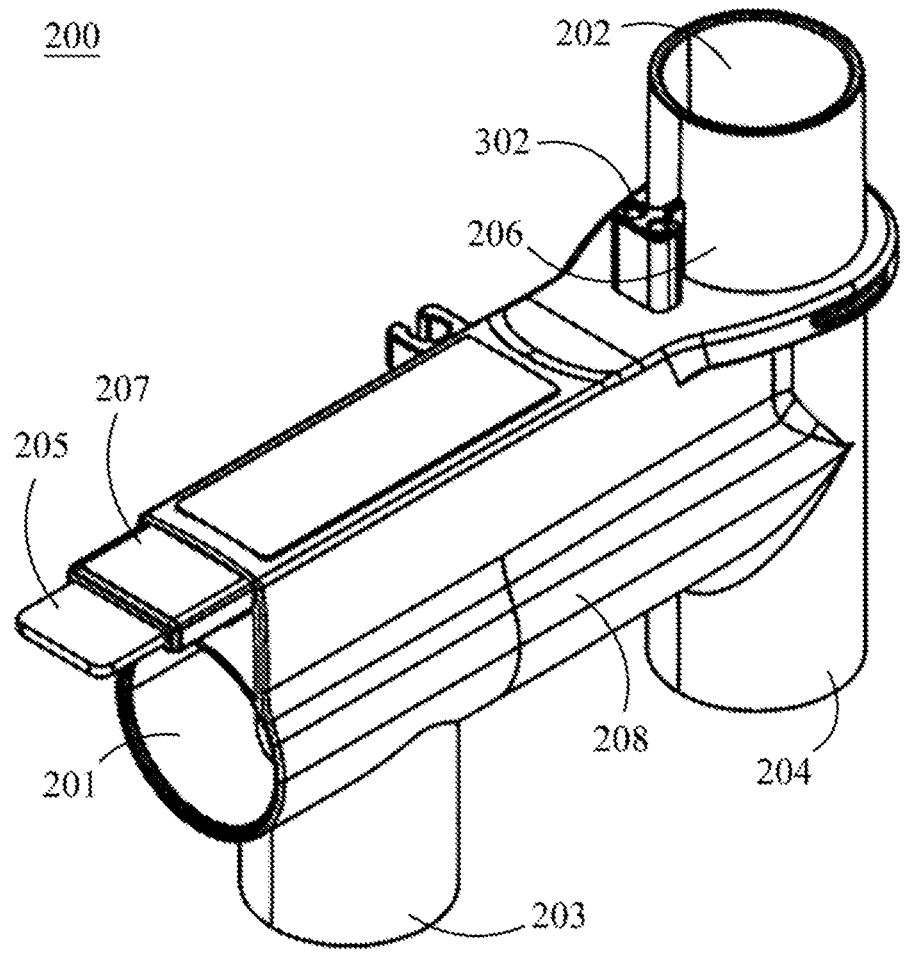
FIG. 2 shows a schematic structural diagram of a chamber adaptor provided by an embodiment of the present application.
Figure 3:
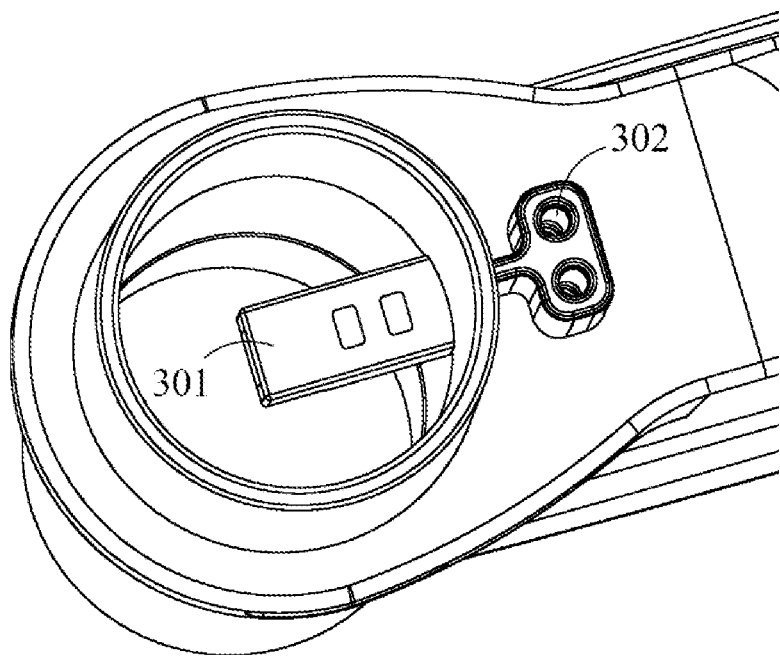
FIG. 3 is a schematic partial structural diagram of a chamber adaptor provided by an embodiment of the present application.

FIG. 2 shows a schematic structural diagram of the chamber adaptor 200 provided by an embodiment of the present application, and FIG. 3 is a schematic partial structural diagram of the chamber adaptor 200 provided by the embodiment of the present application.

As shown in FIG. 2 and FIG. 3, an embodiment of the present application provides a chamber adaptor 200, including: a housing 208 provided with a gas inlet 201, a gas outlet 202, a chamber inlet 203, and a chamber outlet 204, where:

the gas inlet 201 is configured to be removably connected to a main board device (e.g., the main board device 101 shown in FIG. 1), the gas outlet 202 is configured to be removably connected to a respiratory pathway (e.g., the respiratory pathway 104 shown in FIG. 1), the chamber inlet 203 is configured to be removably connected to an input end of a chamber (e.g., the chamber 103 shown in FIG. 1) for storing liquid, and the chamber outlet 204 is configured to be removably connected to an output end of the chamber;

the chamber adaptor 200 further includes a control circuit 205 with at least one sensing apparatus 301 connected to the control circuit 205;

where the at least one sensing apparatus 301 is arranged on one end of the control circuit 205 closer to the gas outlet 202 and extends into a gas output channel 206 formed between the gas outlet 202 and the chamber outlet 204, and the at least one sensing apparatus 301 is configured to detect temperature information of gas passing through the gas output channel 206;

where the other end of the control circuit 205 is electrically connected to the main board device, and the control circuit 205 is configured to deliver the temperature information detected by the at least one sensing apparatus 301 to the main board device.

With reference to FIG. 1 and FIG. 2, the chamber adaptor 200 is configured to direct the gas to flow along a predefined pathway inside the respiratory humidifier 100. Specifically, during operation of the respiratory humidifier 100, the oxygen and compressed air provided by the main board device 101 flow into the chamber adaptor 200 through the gas inlet 201, and then flow out of the chamber adaptor 200 through the chamber inlet 203 into the chamber 103. The gas flowing into the chamber 103 is humidified by the liquid stored in the chamber 103, and then flows out of the chamber 103 back into the chamber adaptor 200 through the chamber outlet 204. The gas output channel 206 is formed between the gas outlet 202 and the chamber outlet 204 to direct the gas to flow from the chamber outlet 204 to the gas outlet 202. The at least one sensing apparatus 301 arranged on one end of the control circuit 205 extends into the gas output channel to detect the temperature information of the gas flowing along the gas output channel 206, and deliver the detected temperature information of the gas to the main board device 101 through the control circuit 205. Finally, the gas flows out of the chamber adaptor 200 into the respiratory pathway 104 through the gas outlet 202.

During the operation of the respiratory humidifier 100, the temperature of the gas flowing through the respiratory humidifier 100 needs to be detected, and the temperature information detected by the sensing apparatus provided in the respiratory humidifier 100 will be fed back to the main board device for optimization of the operating parameters of the respiratory humidifier 100 so as to provide gas with more suitable temperature and humidity to the patient.

In the chamber adaptor 200 provided by the present embodiment, at least one sensing apparatus 301 is arranged on one end of the control circuit 205 to detect the temperature of the gas flowing out from the chamber 103. When the at least one sensing apparatus 301 includes two or more sensing apparatuses, single-point failure of the sensing apparatus can be avoided, that is, as long as one of the sensing apparatuses 301 works normally, the temperature of the gas can be detected and fed back to the main board device 101 in time, thereby improving the accuracy for temperature information detection. It should be noted that the sensing apparatus being arranged closer to the gas outlet 202 and extending into the gas output channel means that the sensing apparatus is arranged on the pathway along which the gas flows out from the chamber 103.

In a possible implementation, a length of the at least one sensing apparatus 301 is within a predefined range.

As shown in FIG. 3, the at least one sensing apparatus 301 extends along the longitude direction of the control circuit 205 into the gas output channel 206. The sensing apparatus 301 is arranged at a predefined length so that the tip of the sensing apparatus 301 is away from the inner surface of the gas output channel 206 for a distance, that is, the tip of the sensing apparatus 301 is right around the middle of the gas output channel 206 and can be fully surrounded by the gas flowing through it, thereby ensuring that the sensing apparatus 301 can detect the temperature of the gas in a more accurate way. In a possible implementation, the tip of the sensing apparatus 301 extends to an axial center line of the gas output channel 206.

In a possible implementation, the at least one sensing apparatus is a thermistor probe. The thermistor probe is an electronic component for temperature detection that has a high sensitivity, wide-range working temperature, small size and high stability, and consequently can detect the temperature in an accurate way.

In a possible implementation, a heat transfer rate between the at least one thermistor probe and the housing 208 is smaller than a heat transfer rate between the at least one thermistor probe and the gas passing through the gas output channel 206.

In practical use, the thermistor probe is not only affected by the temperature of the gas flowing through it, but also is easily affected by the heat transferred between the thermistor probe and the housing 208 of the chamber adaptor 200, and more specifically, between the thermistor probe and the inner surface of the housing 208. Therefore, in the chamber adaptor 200 provided by the present embodiment, a heat transfer rate between the at least one thermistor probe and the housing 208 is set to be smaller than a heat transfer rate between the at least one thermistor probe and the gas passing through the gas output channel 206. The solution can be implemented in various ways, for example, the materials of the thermistor probe and the inner surface of the housing 208 are specifically designed so that there is a high resistance for the heat to transfer between the thermistor probe and the inner surface of the housing 208, so that detection errors caused by the heat transferred between the thermistor probe and the inner surface of the housing 208 can be dramatically reduced, thereby ensuring accuracy of the temperate detection on the gas.

In a possible implementation, the at least one sensing apparatus is connected to the control circuit through a connecting wire, and the connecting wire is arranged on the control circuit in an S shape.

As the sensing apparatus needs to be powered by the electricity supplied by the main board device through the control circuit, the connecting wire needs to be arranged on the control circuit to make the sensing apparatus and the main board device electrically connected. However, the connecting wire is generally made up of a material that has a high thermal conductivity, which will cause errors in gas temperature detection by the sensing apparatus. Therefore, in the chamber adaptor 200 provided by the present embodiment, the connecting wire is arranged in an S shape to extend the length of the connecting wire, so as to slow down the heat transfer rate of the heat transferred along the connecting wire. It shall be noted that the above mentioned S shape refers to that the connecting wire is arranged on the control circuit in a zig-zag route that twists and turns along bends and curves, and the connecting wire arranged in such way benefits from a longer route than that arranged in a straight way.

In a possible implementation, the other end of the control circuit 205 is provided with a preset number of conductive contacts, and the conductive contacts are on the top and the bottom of the control circuit 205, and the conductive contacts are exposed from the control circuit 205.

The control circuit 205 is electrically connected to the main board device through the preset number of conductive contacts provided on the other end of the control circuit 205. In a possible implementation, the control circuit 205 is a printed circuit board assembly (PCBA). In a possible implementation, the conductive contacts provided on the control circuit 205 are "connecting fingers", which serve to plug into a slot in the main board device to realize electrical connection, where the "connecting fingers" generally refer to conductive contacts arranged in a row and hence form a shape of fingers. With such arrangement, since the conductive contacts are on the top and the bottom of the control circuit 205, as long as one side of the control circuit 205 manages to be contacted with the main board device, the main board device can be successfully electrically connected to the circuit board, which increases the stability of power supply.

In a possible implementation, the other end of the control circuit 205 is further provided with a first sealing element formed in a first molding process, and an area of the control circuit 205 where the conductive contacts are located protrudes from the first sealing element. As shown in FIG. 2, the control circuit 205 is fully covered by the first sealing element 207 except for the area where the conductive contacts are located, and the first sealing element 207 may protect the control circuit 205 from interference from the external environment.

In a possible implementation, the gas inlet is isolated from the gas outlet 202 in such a manner that substantially no gas can directly go from the gas inlet 201 to the gas outlet 202 without passing by the chamber inlet 203 and the chamber outlet 204. For example, an airtight wall (not shown) may be set inside a transverse channel (the cylindrical transverse channel located under the control circuit 205 as shown in FIG. 2) of the chamber adaptor to prevent the gas from directly going from the gas inlet 201 to the gas outlet 202 without passing by the chamber inlet 203 and the chamber outlet 204, so that the gas passing through the chamber adaptor can be humidified by the liquid stored in the chamber.

Figure 6:
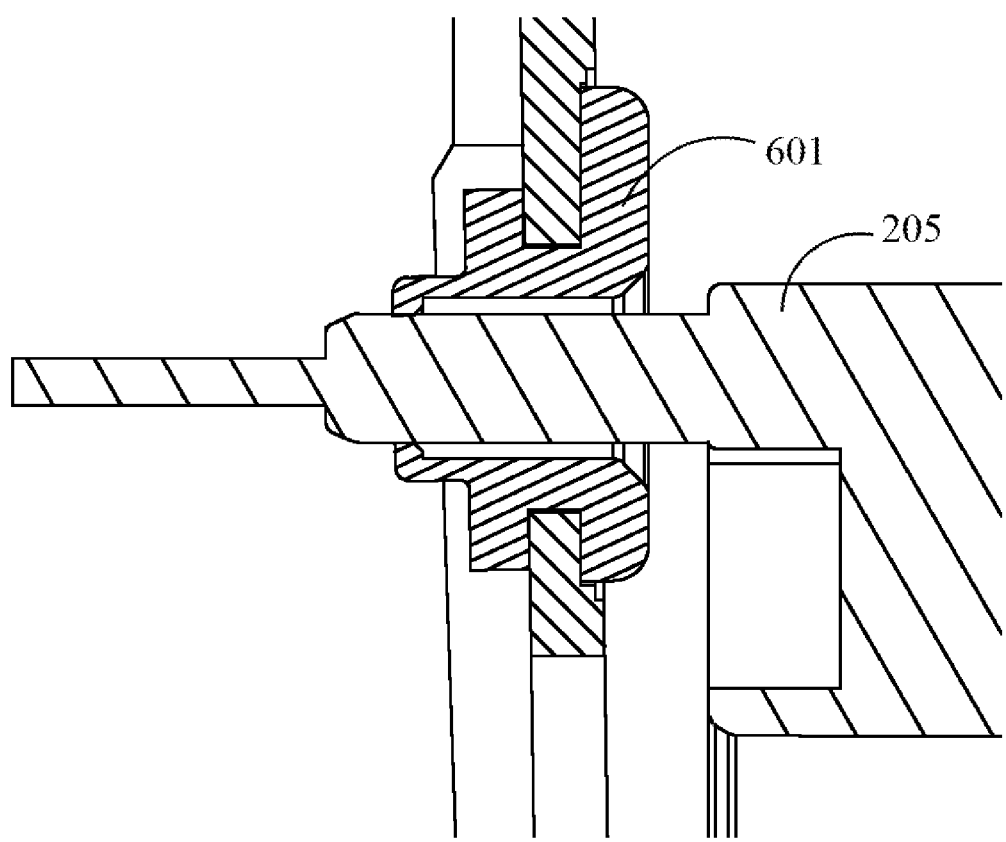
FIG. 6 is a schematic structural diagram of a second sealing element provided by an embodiment of the present application.

In a possible implementation, the other end of the control circuit 205 is provided with a second sealing element 601 (as shown in FIG. 6) to fill a connection gap between the control circuit 205 and the main board device.

As discussed above, the other end of the control circuit can be plugged into the slot of the main board device for electrical connection. As the internal channel of the chamber adaptor is filled with oxygen, compressed air, and vapor generated from the liquid stored in the chamber, although the main body of the control circuit is protected by the first sealing element, the area of the control circuit where the conductive contacts are located is exposed to the environment, and is easy to be affected by the gas leaks from the connection gap between the control circuit 205 and the main board device. Thus a second sealing element 601 may be provided to fill the connection gap between the control circuit 205 and the main board device for further protection.

In a possible implementation, the gas inlet is provided with a one-way valve to prevent the gas flowing from the main board device into the chamber adaptor from flowing back to the main board device, thereby avoiding damages to the devices.

In a possible implementation, the gas inlet is further provided with a third sealing element for preventing gas leakage. Specifically, the third sealing element is provided to fill the connection gap between the gas inlet and the main board device, so that the gas which consists of oxygen and compressed air provided by the main board device to the chamber adaptor will not leak into the external environment.

It should be noted that the first sealing element, the second sealing element 601 and the third sealing element discussed above can be made up of any appropriate materials, as long as they can fulfill their respective functions as discussed above. For example, they can be made up of rubber material which has a good performance in airproof and waterproof.

In a possible implementation, the chamber inlet is a male connector or a female connector, and the chamber outlet is a male connector or a female connector. Specifically, when the chamber inlet is a male connector, the chamber outlet is a female connector; and when the chamber outlet is a female connector, the chamber outlet is a male connector. The female connector will cover the male connector to realize tight connection. Both connection ways can be applied between the chamber adaptor and the chamber as long as effective connection is ensured, which is not limited by the embodiment of the present application.

Figure 4:
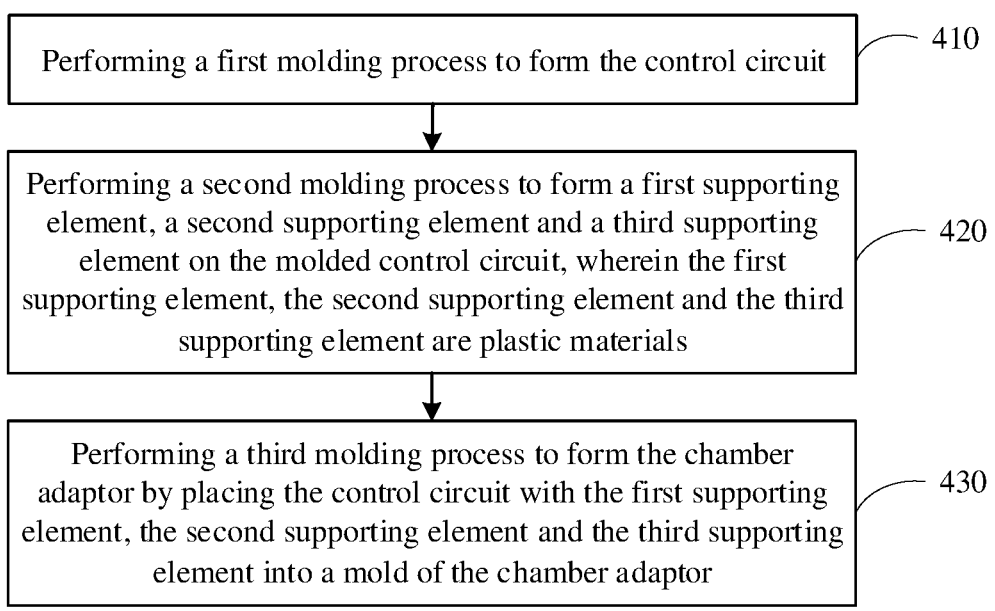
FIG. 4 is a flowchart of a manufacturing method of a chamber adaptor provided by an embodiment of the present application.

An embodiment of the present application provides a method for manufacturing the chamber adaptor according to the embodiments described above. As shown in FIG. 4, the method includes the following steps.

Figure 5:
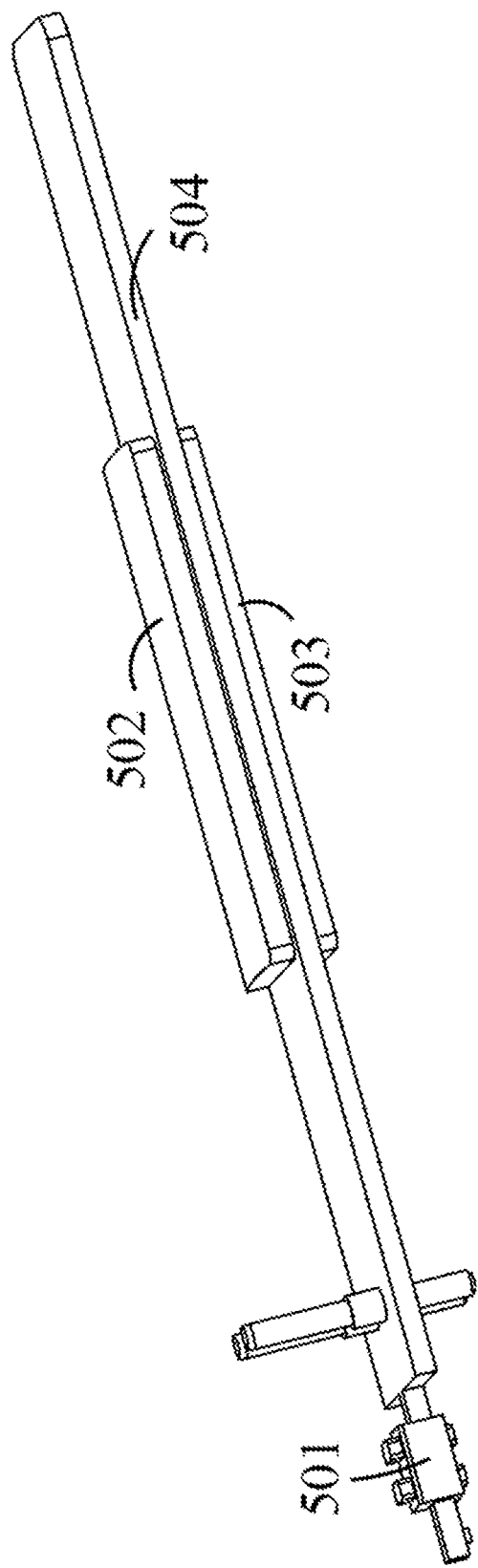
FIG. 5 is a schematic structural diagram of a control circuit with supporting elements provided by an embodiment of the present application.

Step 410: performing a first molding process to form the control circuit. As shown in FIG. 5, the control circuit 504 is formed by performing the first molding process. Here the control circuit can be the control circuit as described above.

Step 420: performing a second molding process to form a first supporting element, a second supporting element and a third supporting element on the molded control circuit, where the first supporting element, the second supporting element and the third supporting element are plastic materials.

Still referring to FIG. 5, the control circuit 504 formed in step 401 does not have a robust strength due to the characteristics of its structure, thus the first supporting element 501, the second supporting element 502 and the third supporting element 503 are formed on the control circuit to prevent the control circuit from warping caused by the high strength generated by the flowing colloid within the mold. The control circuit formed in step 420 has a higher strength due to the supporting elements.

Step 430: performing a third molding process to form the chamber adaptor by placing the control circuit with the first supporting element, the second supporting element and the third supporting element into a mold of the chamber adaptor.

Finally, the control circuit formed in step 420 is placed into the mold of the chamber adaptor to form the chamber adaptor as discussed in the above embodiments.

It should be understood by a person skilled in the art that, the relevant description of the above steps in the embodiments of the present application may be understood with reference to the relevant description of the method for monitoring a condition of a patient in the embodiments of the present application.

The term such as "and/or" in the embodiments of the present application is merely used to describe an association between associated objects, which indicates that there may be three relationships, for example, A and/or B may indicate presence of A only, of both A and B, and of B only.

The term "a" or "an" is not intended to specify one or a single element, instead, it may be used to represent a plurality of elements where appropriate.

In the embodiments of the present application, expressions such as "exemplary" or "for example" are used to indicate illustration of an example or an instance. In the embodiments of the present application, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

It should be appreciated that, steps may be reordered, added, or deleted according to the various processes described above. For example, the steps described in the present application may be executed in parallel, sequentially, or in different orders, which are not limited herein as long as the desired results of the technical solutions disclosed in the present application can be achieved.

Finally, it should be noted that the foregoing embodiments are merely intended for describing the technical solutions of the present invention other than limiting the present invention. Although the present invention is described in detail with reference to the foregoing embodiments, a person of ordinary skill in the art should understand that he may still make modifications to the technical solutions described in the foregoing embodiments, or make equivalent replacements to some technical features thereof, without departing from the spirit and scope of the technical solutions of the embodiments of the present invention.

What is claimed is:

1. A chamber adaptor, comprising a housing provided with a gas inlet, a gas outlet, a chamber inlet, and a chamber outlet; wherein:
    the gas inlet is configured to be removably connected to a main board device, the main board device is configured to provide oxygen and compressed air to the chamber adaptor, the gas outlet is configured to be removably connected to a respiratory pathway, the chamber inlet is configured to be removably connected to an input end of a chamber for storing liquid and the chamber outlet is configured to be removably connected to an output end of the chamber;
    the chamber adaptor further comprises a control circuit having a first end and a second end that are opposite to each other, and a distance between the first end and the second end is a total length of the control circuit;
    wherein the at least one sensing apparatus is provided at the first end of the control circuit and extends into a gas output channel formed between the gas outlet and the chamber outlet, the space defined by an inner wall of the gas output channel only comprises the at least one sensing apparatus, and the at least one sensing apparatus is configured to detect a temperature of the gas passing through the gas output channel;
    wherein a second end of the control circuit is electrically connected to the main board device, and the control circuit is configured to deliver the temperature detected by the at least one sensing apparatus to the main board device;
    wherein a first supporting element, a second supporting element, and a third supporting element are formed on the control circuit, and the first supporting element, the second supporting element, and the third supporting element are all in contact with a surface of the control circuit, so as to improve a strength of the control circuit and support the circuit board within a mold of the chamber adaptor to prevent the control circuit from warping.

2. The chamber adaptor according to claim 1, wherein a length of the at least one sensing apparatus is within a predefined range.

3. The chamber adaptor according to claim 1, wherein the at least one sensing apparatus is connected to the control circuit through a connecting wire, and the connecting wire is arranged on the control circuit in an S shape.

4. The chamber adaptor according to claim 1, wherein the second end of the control circuit is provided with a preset number of conductive contacts, and the conductive contacts are on the top and the bottom of the control circuit, and the conductive contacts are exposed from the control circuit.

5. The chamber adaptor according to claim 4, wherein the second end of the control circuit is further provided with a first sealing element formed in a first molding process, and an area of the control circuit where the conductive contacts are located protrudes from the first sealing element.

6. The chamber adaptor according to claim 1, wherein the gas inlet is isolated from the gas outlet in such a manner that substantially no gas can directly go from the gas inlet to the gas outlet without passing by the chamber inlet and the chamber outlet.

7. The chamber adaptor according to claim 1, wherein the second end of the control circuit is provided with a second sealing element to fill a connection gap between the control circuit and the main board device.

8. The chamber adaptor according to claim 1, wherein the gas inlet is provided with a one-way valve.

9. The chamber adaptor according to claim 8, wherein the gas inlet is further provided with a third sealing element for preventing gas leakage.

10. The chamber adaptor according to claim 1, wherein the chamber inlet is a male connector or a female connector, and the chamber outlet is a male connector or a female connector.

11. The chamber adaptor according to claim 2, wherein the at least one sensing apparatus is a thermistor probe.

12. The chamber adaptor according to claim 11, wherein a heat transfer rate between the at least one thermistor probe and the housing is smaller than a heat transfer rate between the thermistor probe and the gas passing through the gas output channel.

* * * * *